US008784429B2

(12) United States Patent  (10) Patent No.: US 8,784,429 B2
Bryan et al.  (45) Date of Patent: Jul. 22, 2014

(54) DISTANCE INDICATOR

(76) Inventors: Jason A. Bryan, Avon Lake, OH (US);
Joseph P. Iannotti, Strongsville, OH (US); Wael K. Barsoum, Bay Village, OH (US)

( * ) Notice: Subject to any disclaimer, the term of this patent is extended or adjusted under 35 U.S.C. 154(b) by 0 days.

(21) Appl. No.: 13/348,034

(22) Filed: Jan. 11, 2012

(65) Prior Publication Data
US 2012/0203237 A1 Aug. 9, 2012

Related U.S. Application Data

(60) Provisional application No. 61/431,472, filed on Jan. 11, 2011.

(51) Int. Cl.
*A61B 17/58* (2006.01)
*A61B 17/60* (2006.01)
*A61F 2/00* (2006.01)

(52) U.S. Cl.
USPC ............ 606/102; 606/103; 606/104; 606/96; 606/99

(58) Field of Classification Search
USPC ................................ 606/102, 103, 104, 96, 99
See application file for complete search history.

(56) References Cited

U.S. PATENT DOCUMENTS

| 1,459,896 A | * | 6/1923 | John .............................. 33/544 |
| 2,243,718 A |  | 5/1941 | Moreira |
| 4,004,581 A |  | 1/1977 | Heimke et al. |
| 4,519,144 A | * | 5/1985 | Larsen ......................... 33/199 R |
| 5,180,388 A |  | 1/1993 | DiCarlo |
| 5,197,967 A |  | 3/1993 | Wilson |
| 5,458,604 A |  | 10/1995 | Schmieding |
| 5,895,389 A |  | 4/1999 | Schenk et al. |
| 7,207,995 B1 |  | 4/2007 | Vandewalle |
| 2003/0181920 A1 |  | 9/2003 | Hawkins et al. |
| 2009/0254094 A1 |  | 10/2009 | Knapp et al. |
| 2012/0330323 A1 | * | 12/2012 | Lizardi et al. ................. 606/102 |

OTHER PUBLICATIONS

U.S. Appl. No. 61/362,722, filed Jul. 9, 2010, and titled "Method and Apparatus for Providing a Relative Location Indication During a Surgical Procedure".
The PCT Int'l Search Report dated May 8, 2012 for PCT Int'l Appln. No. PCT/US2012/020898, filed Jan. 11, 2012, pp. 1-16.

* cited by examiner

*Primary Examiner* — Andrew Yang
*Assistant Examiner* — Olivia C Chang
(74) *Attorney, Agent, or Firm* — Norton Rose Fulbright Canada LLP

(57) ABSTRACT

A distance indicator for indicating the distance that a device has traveled includes an elongate housing with a guidewire connector configured for operative connection to a guidewire to hold the housing stationary with respect thereto. A plunger is operatively connected to the housing for longitudinal motion with respect to the housing. A first plunger end is configured to operatively contact the device. As the guidewire connector is holding the housing stationary with respect to the guidewire, the first plunger end is placed into operative contact with the device with the plunger and housing in a first relative plunger/housing position. The device moves longitudinally. The plunger moves into a second relative plunger/housing position assisted by the operative connection between the first plunger end and the device. The longitudinal difference between the first and second relative plunger/housing positions indicates a distance that the device has moved longitudinally with respect to the guidewire.

14 Claims, 4 Drawing Sheets

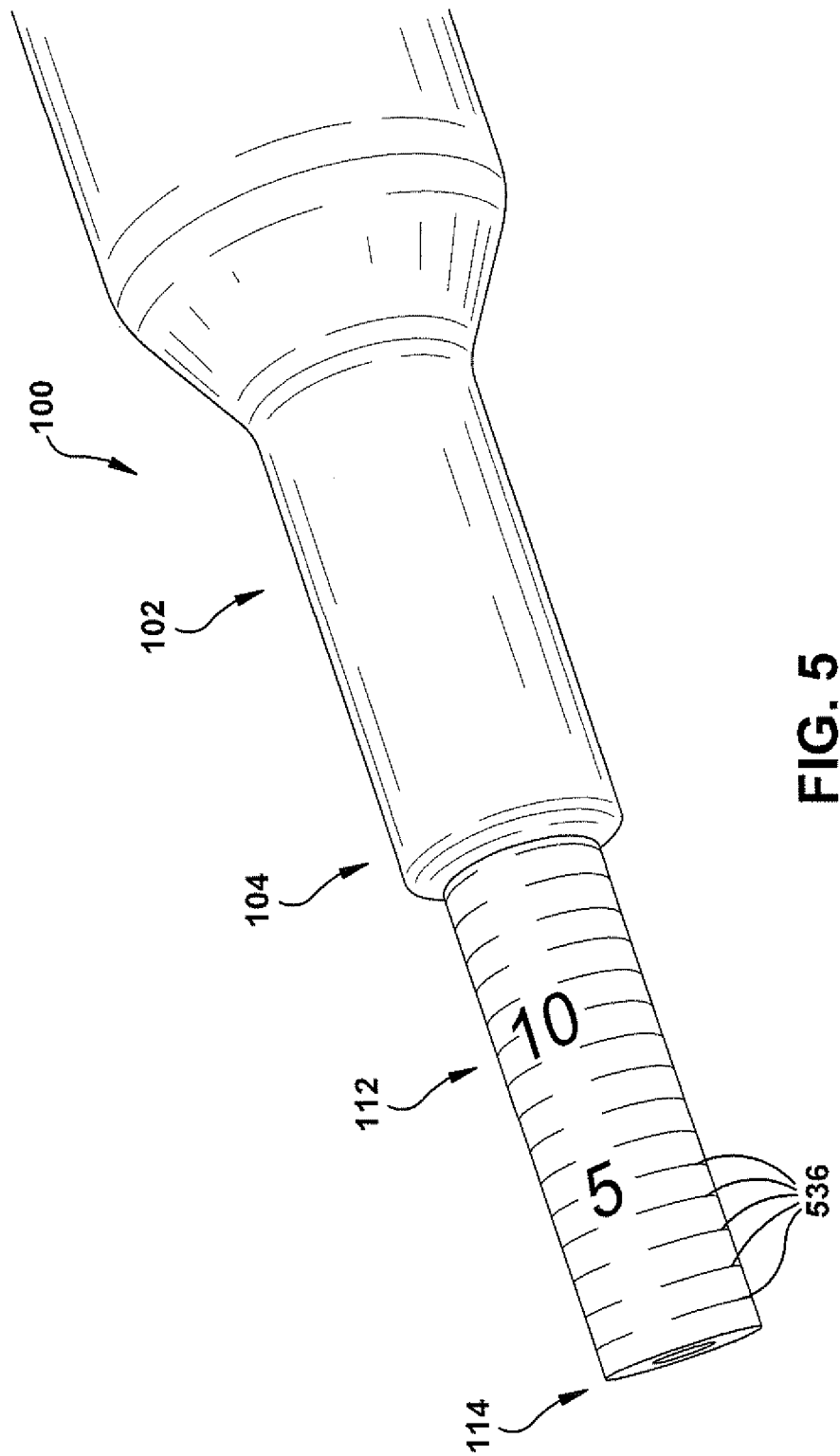

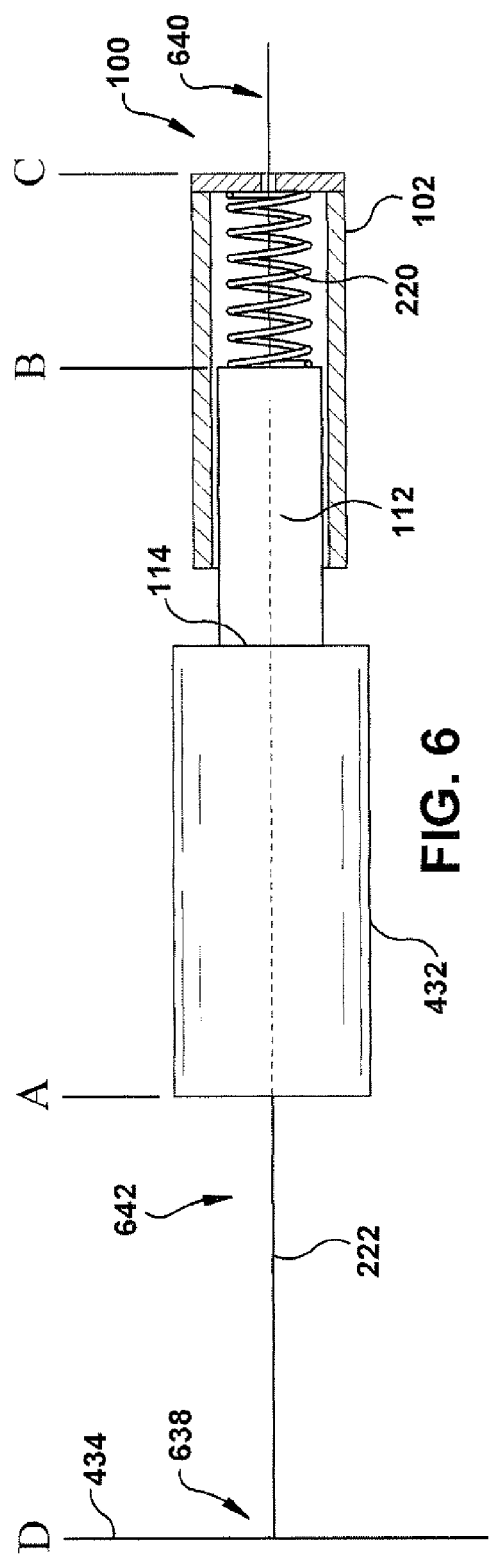
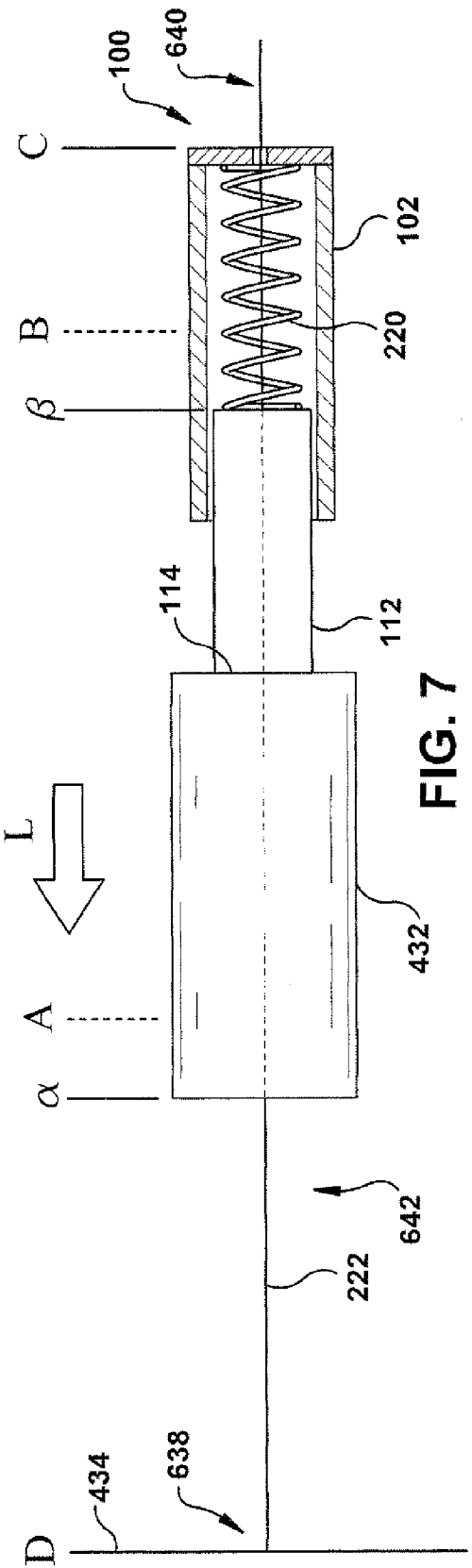

DISTANCE INDICATOR

RELATED APPLICATION

This application claims priority from U.S. Provisional Application No. 61/431,472, filed 11 Jan. 2011, the subject matter of which is incorporated herein by reference in its entirety.

TECHNICAL FIELD

The present invention relates to an apparatus and method for use of a distance indicator and, more particularly, to a distance indicator for monitoring movement of a device with respect to a stationary reference.

BACKGROUND OF THE INVENTION

It is sometimes desirable, during surgery, for a user to place a marking/guide pin, guiding wire, or other elongate marker (hereafter referenced as a "guidewire") into penetrating engagement with a patient tissue. This "landmarking" via a guidewire may be helpful, for example, during orthopedic surgery. One example of a suitable guidewire is disclosed in co-pending U.S. Provisional Patent Application Ser. No. 61/362,722, filed Jul. 9, 2010, and titled "Method and Apparatus for Providing a Relative Location Indication During a Surgical Procedure", the contents of which are hereby incorporated by reference in their entirety.

Once the guidewire has been placed in a desired location, and, optionally, at a desired trajectory, a cannulated tool (e.g., a drill), implant (e.g., a bone screw, acetabular component, glenoid component, bone plate, or the like), and/or other component (hereafter, "device") may be passed over the guidewire and guided into contact with the patient tissue as desired. One skilled in the art will readily appreciate that a cannulated device refers to a device having a small diameter through-passage throughout at least a portion of the entire length of the device, optionally coaxial with the device, that can be configured to insert a guidewire therethrough.

One aspect of surgery in which a guidewire may be helpful is in guiding a cannulated drill into a patient tissue (e.g., a bone tissue) to create an aperture having a desired location and trajectory. However, the user often will also desire the aperture to have a particular depth (i.e., distance of insertion of the drill bit into the patient tissue). This measurement may be particularly important when the user is striving to avoid complete penetration and "punching through" the body tissue.

In the field, the insertion depth has been difficult to determine interoperatively from mere visual observation of a penetrating device, either in cannulated/wire-guided or "freehand" operation modes. Several prior art depth indicators have been proposed as aids to determine insertion depth of a device into a patient tissue. These depth indicators tend to be one of two styles: a simple probe inserted into the aperture in the patient tissue to directly measure depth, or a measuring structure attached to the device and contacting the patient tissue beside the aperture. Both of these styles have disadvantages. The former style requires removal of the device from the aperture before measuring can take place, and thus real-time measurement cannot occur. The latter style presumes that the nearby patient tissue is the same distance from the tool as the patient tissue being penetrated (which is not always the case) and also often is device-specific and not useful with a variety of devices. Another drawback to these two prior art device styles is that direct contact with the patient tissue is required, which could lead to patient tissue damage and/or contamination.

SUMMARY OF THE INVENTION

In an embodiment of the present invention, a distance indicator for indicating the distance that a device has traveled with respect to a guidewire is described. An elongate housing has first and second housing ends longitudinally separated by a housing body and a guidewire connector configured for operative connection to the guidewire to hold the housing stationary with respect thereto. A plunger has first and second plunger ends longitudinally separated by a plunger body. The plunger is operatively connected to the housing for longitudinal motion with respect to the housing. The first plunger end is configured to operatively contact the device. A biasing member urges the plunger longitudinally with respect to the housing to keep the first plunger end in operative contact with the device as the device moves with respect to the guidewire. As the guidewire connector is holding the housing stationary with respect to the guidewire, the first plunger end is placed into operative contact with the device with the plunger and housing in a first relative plunger/housing position. The device moves longitudinally with respect to the guidewire and attached housing. The plunger moves into a second relative plunger/housing position assisted by the operative connection between the first plunger end and the device. The longitudinal difference between the first and second relative plunger/housing positions indicates a distance that the device has moved longitudinally with respect to the guidewire.

In an embodiment of the present invention, a method for monitoring movement of a device with respect to a stationary reference is described. A distance indicator is provided, the distance indicator including an elongate housing having first and second housing ends longitudinally separated by a housing body, and a plunger having first and second plunger ends longitudinally separated by a plunger body, the plunger being operatively connected to the housing for longitudinal motion with respect to the housing. The distance indicator is operatively connected to the stationary reference to hold the housing stationary with respect to the stationary reference. The first plunger end is operatively connected to the device in a first relative plunger/housing position. The device is moved longitudinally with respect to the stationary reference. The plunger is urged longitudinally with respect to the housing to keep the first plunger end in operative contact with the device as the device moves with respect to the stationary reference. The plunger is moved into a second relative plunger/housing position assisted by the operative connection between the first plunger end and the device. A distance that the device has moved longitudinally with respect to the stationary reference is indicated by the longitudinal difference between the first and second relative plunger/housing positions.

In an embodiment of the present invention, an apparatus for monitoring movement of a device with respect to a patient tissue is provided. The device is connected to the patient tissue by a guidewire having first and second guidewire ends longitudinally separated by a guidewire body. The first guidewire end contacts the patient tissue and the device is located longitudinally between the first and second guidewire ends and is movably connected to the guidewire. An elongate housing has first and second housing ends longitudinally separated by a housing body. A guidewire connector is configured to accept at least one of the guidewire body and the second guidewire end to hold the housing stationary with respect thereto. A plunger has first and second plunger ends longitudinally separated by a plunger body. The plunger is operatively connected to the housing for longitudinal motion with respect to the housing. The first plunger end is configured to operatively contact the device in a first relative plunger/housing position. A biasing member urges the plunger longitudinally with respect to the housing to keep the first plunger end in operative contact with the device as the device moves with respect to the guidewire. The biasing member is configured to move the plunger into a second relative plunger/housing position assisted by the operative connection between the first plunger end and the device. The longitudinal difference between the first and second relative plunger/housing positions indicates a distance that the device has moved longitudinally with respect to the guidewire.

BRIEF DESCRIPTION OF THE DRAWINGS

For a better understanding of the invention, reference may be made to the accompanying drawings, in which:

FIG. 5 is a partial perspective side view showing an alternate arrangement for one portion of the embodiment of FIG. 1; and FIGS. 6-7 illustrate a sequence of operation of the embodiment of FIG. 1.

DESCRIPTION OF EMBODIMENTS

Figure 1:
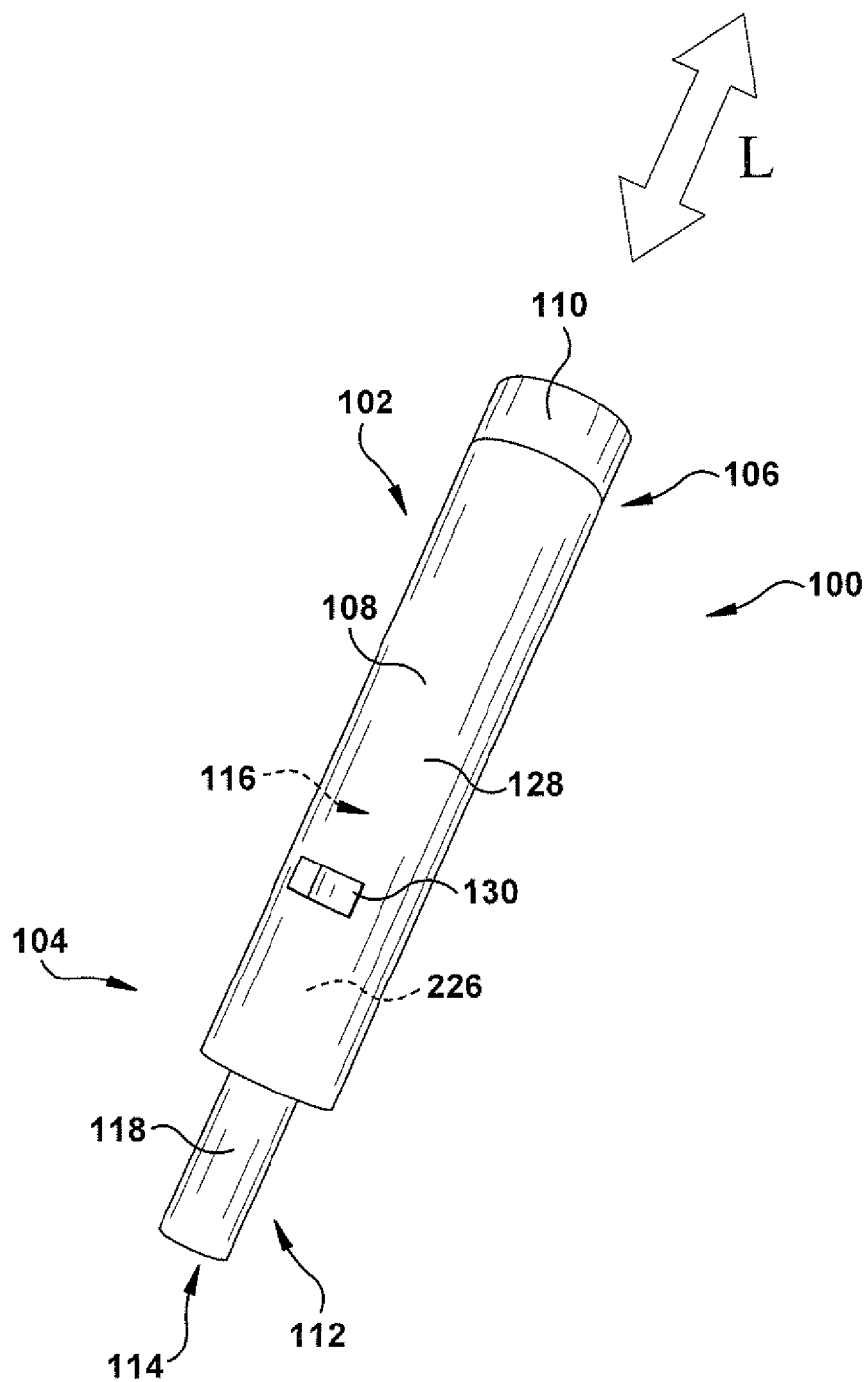
FIG. 1 is a perspective side view of one embodiment of the present invention.

In accordance with the present invention, FIG. 1 depicts a distance indicator 100 for indicating the distance that a device has traveled with respect to a guidewire. The use environment will be described herein as being a medical use environment, wherein a device is penetrating into a relatively stationary patient tissue, but could be any suitable environment in which a device moves in at least one dimension toward or away from a relatively stationary substrate.

The term "device" is used herein to indicate a tool, component, implant, or other item having a one-dimensional displacement (i.e., in a "primary dimension", such as longitudinal direction L shown in the Figures) that a user wishes to measure. The term "guidewire" is used herein to indicate a relatively slender, elongate structure which is fixed in the primary dimension with respect to a patient tissue and extends outward from a patient tissue while the device is being used. It is contemplated that, for most embodiments of the present invention, the guidewire will extend from the patient tissue in the primary dimension and terminate at a location at least as far from the patient tissue in that primary dimension as the location at which a device is initially placed to interact with the patient tissue.

The distance indicator 100 includes an elongate housing 102 having first and second housing ends 104 and 106, respectively, longitudinally separated by a housing body 108, as shown in FIG. 1. A guidewire connector 110 is configured for operative connection to a guidewire (not shown in FIG. 1) to hold the housing 102 substantially stationary with respect to the guidewire.

A plunger 112 has first and second plunger ends 114 and 116 (located within the housing 102 in FIG. 1), respectively, longitudinally separated by a plunger body 118. The plunger 112 is operatively connected to the housing 102 for longitudinal motion with respect to the housing. The first plunger end 114 is configured to operatively contact the device for which the movement distance is being measured, as will be described below.

Figure 2:
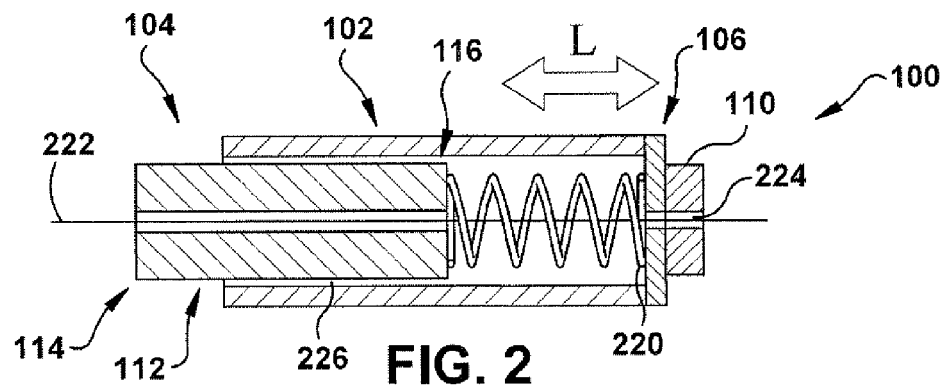
FIG. 2 is a schematic sectional side view of the embodiment of FIG. 1 in a first configuration.

With reference to FIG. 2, a biasing member 220 urges the plunger 112 longitudinally with respect to the housing 102 to keep the first plunger end in operative contact with the device as the device moves with respect to the guidewire (222 in the Figures). Depending upon the configuration of the distance indicator 100 and its relationship to the device, the biasing member 220 may urge the plunger 112 longitudinally toward or longitudinally away from the housing 102. The biasing member 220 is shown schematically as a spring in the Figures, but may be of any suitable type, such as, but not limited to, a spring, hydraulic actuator, pneumatic actuator, vacuum line, fluid pressure line, shape memory material structure, magnetic force, gravitational force, or any other means for exerting an appropriate force between the plunger 112 and the housing 102. During operation of the distance indicator 100, the plunger 112 and guidewire 222 begin at a first relative plunger/housing position, then, as the device moves with respect to the guidewire, the biasing member 220 similarly urges the plunger 112 to move with respect to the housing 102 to at least one other relative plunger/housing position. This latter plunger/housing position is referenced herein as being a "second" plunger/housing position, but as will be explained below, the "second" plunger/housing position need not be a terminal plunger/housing position. In fact, the plunger 112 and housing 102 could move through the "second" plunger/ housing position without pause, or with merely a brief pause, as desired by the user.

The guidewire connector 110 is shown schematically in the Figures. The guidewire connector 110 may be of any suitable type configured and operative to hold the housing 102 in a relatively longitudinally fixed relationship with the guidewire 222. For example, and as shown in FIG. 2, a guidewire aperture 224 may extend at least a portion of the longitudinal distance through the guidewire connector 110. When present, the guidewire aperture 224 may serve to accept the guidewire 222 and place the housing 102 into a desired guidewire/ housing position.

As another option, the guidewire connector 110 may frictionally engage the guidewire 222 to hold the housing 102 in the relatively longitudinally fixed relationship with the guidewire 222 as described. For example, a guidewire aperture 224 could be provided which has a slightly smaller diameter than the guidewire 222 and requires that the guidewire be forced into the guidewire aperture. As another example, at least a portion of the guidewire connector 110 may be made from a resilient and/or adhesive material which grips the guidewire 222 when brought into contact therewith under sufficient coupling force. One more example of a suitable guidewire connector 110 includes a clip (not shown) that can be selectively opened and closed by a user to grip and release, respectively, the guidewire 222. Depending upon the length of the guidewire 222, the guidewire connector 110 could engage directly with a terminal or free end of the guidewire, opposite the patient tissue.

The guidewire connector 110 is shown in the Figures as being located in direct contact with the second housing end 106 for ease of description, but may be located in any orientation, directly contacting or spaced apart from other structures of the distance indicator 100. It is also contemplated that multiple guidewire connectors 110 could be provided to a single distance indicator 100; for example, there could be means provided at or near both the first and second housing ends 104 and 106 to serve as guidewire connectors and maintain the housing 102 and guidewire 222 in the desired guidewire/housing relationship. The guidewire connector 110, regardless of its specific structure or relationship to other components of the distance indicator 100, should be configured to resist relative motion between the guidewire 222 and the housing 102 when the housing and guidewire are in the desired guidewire/housing position and during use of the distance indicator.

As shown in FIG. 2, the housing 102 could include a plunger aperture 226 extending from the first housing end 104 into the housing body 108. When present, the plunger aperture 226 may accept the second plunger end 116 and at least a portion of the plunger body 118 and allow relative motion of the plunger 112 either toward or away from the second housing end 106 during movement of the plunger from the first relative plunger/housing position to the second relative plunger/housing position, depending upon the direction of motion of the device with respect to the guidewire 222.

Figure 3:
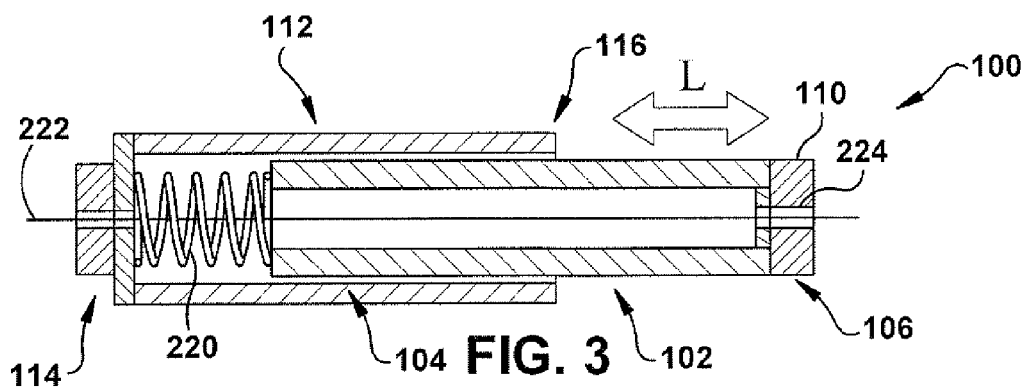
FIG. 3 is a schematic sectional side view of the embodiment of FIG. 1 in a second configuration.

The distance indicator 100 shown in FIG. 3 differs mainly from that in FIG. 2 in the arrangement of components. While the FIG. 2 configuration has a plunger 112 at least partially located within a housing 102, the FIG. 3 configuration is reversed, with the housing at least partially located within the plunger. Either of these configurations, and any others which provide distance indication as described, are contemplated by the present invention.

Figure 4:
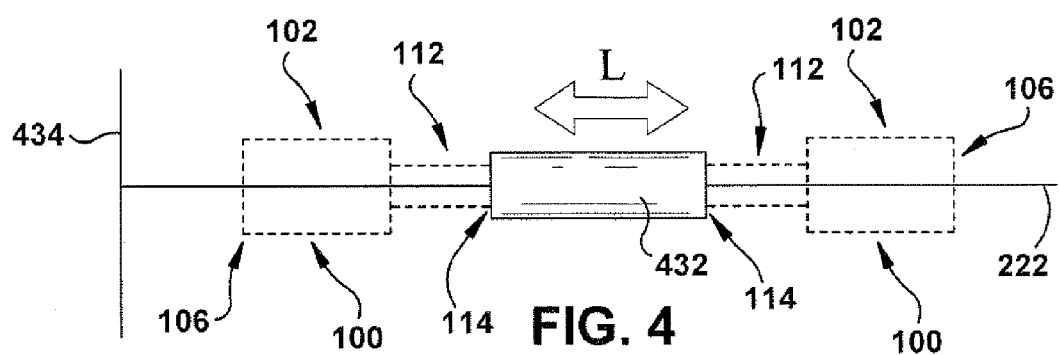
FIG. 4 is a schematic side view of the embodiment of FIG. 1 in an example use environment.

FIG. 4 illustrates schematically that the distance indicator 100 can be located either between a device 432 and a patient tissue 434 (i.e., to the left in the orientation of FIG. 4), or the distance indicator can be located on a longitudinally opposite side of the device from the patient tissue (i.e., to the right in the orientation of FIG. 4). For most applications of the present invention, the distance indicator 100 will function agnostic of its spatial relationship with the device 432 and the guidewire 222, and one of ordinary skill in the art can readily configure the plunger 112, housing 102, and other structures of the distance indicator for use in either position. However, it is contemplated that the user may want to avoid the interposition of a structure such as the distance indicator 100 between the device 432 and the patient tissue 434. Therefore, the below description presumes that the distance indicator 100 will be located on the longitudinally opposite side of the device from the patient tissue (i.e., to the right in the orientation of FIG. 4).

With reference to FIG. 1, the plunger aperture 226 is in at least one of visual and fluid communication with an outer surface 128 of the housing 102 through a viewing aperture 130 extending substantially laterally through at least a portion of the housing body 108. The viewing aperture 130 allows a user to visualize a position, usually a longitudinal position, of the plunger within the housing body 108. This position visualization may be binary, in which the user can just see whether enough of the plunger 112 is contained within the plunger aperture 226 so that the second plunger end 116 or a portion of the plunger body 118 can be seen through the viewing aperture. The position visualization may also be scalar, in which at least one visible mark inscribed on the plunger 112 can be seen through the viewing aperture. In this latter instance, the plunger 112 could include a series of visible marks, and the user could use these visible marks to quantify the physical relationship of the plunger 112 and the housing 102 more precisely than in the binary position visualization. This position visualization, regardless of the manner in which it is accomplished, may be helpful in indicating to the user the change in relative position between the plunger 112 and the housing 102 between the first and second relative plunger/housing positions.

FIG. 5 shows an alternate arrangement for indicating to a user the physical relationship of the plunger 112 and the housing 102, again by providing an indicator scale to at least one of the plunger and the housing. In FIG. 5, the plunger 112 is provided with a series of visible marks 536 (only a subset of which are numbered, for clarity) which together form an indicator scale configured to provide a quantitative indication of the longitudinal distance traveled by the plunger with respect to the housing 102 during movement of the plunger from the first relative plunger/housing position to the second relative plunger/housing position. For example, the user could see on the indicator scale that the number "5" visible mark 536 is the rightmost (in the orientation of FIG. 5) visible mark protruding from the first housing end 104 when the distance indicator 100 is in the first relative plunger/housing position. The plunger 112 is then moved (e.g., is pulled outward from the plunger aperture 226) to place the distance indicator 100 in the second relative plunger/housing position, at which time it might be observed that the number "15" visible mark 536 has become the rightmost (in the orientation of FIG. 5) visible mark protruding from the first housing end 104, as shown in FIG. 5. Accordingly, the distance indicator 100 would then be quantitatively indicating to the user that the distance between the first and second relative plunger/housing positions is 10 units, in whatever numerical system—standard (e.g., millimeters or inches) and/or task-specific—the indicator scale uses.

An example mode of operation of the distance indicator 100 will now be discussed, with reference to the sequence of FIGS. 6-7. This sequence shows schematically an example in which the guidewire 222 has first and second guidewire ends 638 and 640 longitudinally separated by a guidewire body 643. The first guidewire end 638 contacts the patient tissue 434, and may penetrate some distance into the patient tissue to maintain the guidewire 222 in a desired position. The device 432 is movably connected to the guidewire 222—a relatively stationary reference structure—in such a manner as to allow longitudinal motion of the device toward or away from the patient tissue 434.

In FIG. 6, the guidewire connector 100 has been engaged to hold the housing 102 stationary with respect to the guidewire 222 and the first plunger end 114 has been placed into operative contact with the device 432 with the plunger 112 and the housing 102 in the first relative plunger/housing position. This operative contact between the first plunger end 114 and the device 432 could be as simple as a touching of the surface of one to the other, and/or could be aided by an adhesive; a mounting bracket, hook, or other mechanical coupler; or any other means for attaching the first plunger end 114 to the device 432. Here, the biasing member 220 urges the plunger 112 toward the left, in the orientation of FIGS. 6 and 7, to keep the first plunger end 114 in the operative contact with the device 432. With the plunger 112 and the housing 102 in the first relative plunger/housing position, the user may desire to visually observe, mark, or in any other manner record a quantitative measurement of the first relative plunger/housing position, optionally with the assistance of a provided indicator scale (not shown). In FIG. 6, reference line "A" marks the longitudinal position of the device 432, reference line "B" marks the longitudinal position of the second plunger end 116, reference line "C" marks the longitudinal position of the second housing end 106, and reference line "D" marks the longitudinal position of the patient tissue 434. The biasing member 220 can be seen to be in a compressed state, as shown schematically in FIG. 6.

The device 432 is then moved longitudinally (in direction "L") with respect to the patient tissue 434, as shown in FIG. 7. For example, if a cannulated drill is the device 432 and is being guided by the guidewire 222 to drill an aperture into the patient tissue 434, the cannulated drill will move to the left, in the orientation of FIGS. 6 and 7. Since the guidewire 222 and housing 102 are relatively fixed with respect to the patient tissue 434, only the plunger 112 and device 432 will move in the depicted scenario. This movement is visually indicated in FIG. 7 by the device 432 moving from reference line "A" to reference line "α", and the second plunger end 114 moving from reference line "B" to reference line "β" while the second housing end 106 remains at reference line "C" and the patient tissue 434 remains at reference line "D".

As is shown schematically in FIG. 7, the biasing member 220 has expanded longitudinally to urge the plunger 112 longitudinally with respect to the housing 102, telescoping these portions of the distance indicator 100 outward, and thereby keep the first plunger end 114 in operative contact with the device 432. In some configurations of the present invention, the biasing member 220 may instead be a mechanical connection (not shown) between the first plunger end 114 and the device 432 that pulls the plunger 112 along with the device to provide the depicted motion of the plunger with respect to the housing 102.

Regardless of the manner in which the plunger 112 is urged longitudinally, the distance indicator 100 has been moved into the second relative plunger/housing position in the view of FIG. 7, in which the plunger 112 has telescoped outward from the housing 102. The user can then observe the longitudinal difference (here, the distances A-α and B-β) between the first and second relative plunger/housing positions and thereby deduce a distance that the device 432 has moved longitudinally with respect to the guidewire 222, and hence with respect to the patient tissue 434. Unless gearing means of some type are present (not shown here) to change the component travel ratios, the distances A-α and B-β will normally be substantially equal to each other and equal to the amount that the device 432 has moved with respect to the patient tissue 434.

When present, the indicator scale may assist with quantifying this movement distance of the device 432. For example, if the longitudinal movement of the cannulated drill device 432 is shown by the distance indicator to be two inches, the user will know that the aperture in the tissue has been made two inches deeper by movement of the drill device. This may be helpful in procedures where an initial observation (i.e., the distance indicator 100 is in the first relative plunger/housing position) is made with the drill bit tip just touching the patient tissue 434 surface, and then a later observation (i.e., the distance indicator 100 is in the first relative plunger/housing position) is made with, the drill bit tip penetrating into the patient tissue surface. The distance indicator 100 gives the user a real-time view of the depth of insertion of the drill (or other device 432) into the patient tissue 434, without requiring removal of the drill and/or direct contact with the patient tissue, as in the prior art devices. The user can stop drilling (or otherwise moving the device 432) to check the distance traveled, or can monitor the distance continually during movement of the device.

It is contemplated that the present invention may be used without a guidewire 222, as long as some reference structure extends from a substrate (such as the described patient tissue 434) longitudinally toward and/or beyond a longitudinally moving device. The reference structure should be relatively stationary with respect to the substrate. For example, the distance indicator 100 could be designed to ride along a wall extending substantially perpendicular to a substrate being approached or retreated from by a device.

It is also contemplated that the distance indicator 100, or portions thereof (e.g., the plunger 112) could contact the patient tissue 434 or other substrate directly during all or part of the distance indication process. For example, the second housing end 106 could directly contact the patient tissue 434 and the first plunger end 114 could directly contact a structure of the device 432, so that the plunger 112 and housing 102 can relatively telescope inward or outward as the device moves, with or without the aid of a guidewire 222.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system are merely illustrative; one of ordinary skill in the art could readily determine any number or type of components, sequences of steps, or other means/options for measuring a distance in a manner substantially similar to those shown and described herein. Any of the described structures and components could be integrally formed as a single piece or made up of separate sub-components, with either of these formations involving any suitable stock or bespoke components and/or any suitable material or combinations of materials. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. The distance indicator 100 could be used with a bone screw or other medical implant, or with any other device 432 that moves longitudinally with respect to a substrate. The distance indicator 100 could be at least partially disposable or intended for one-time use, possibly by including a sacrifice feature (not shown) rendering the distance indicator unusable after an initial use—this may be particularly helpful in a medical use environment if the distance indicator is not intended for repeat sterilization and reuse. A "stop" component could be used in conjunction with the distance indicator 100 to prevent longitudinal motion of the device 432 above a certain amount. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A distance indicator for indicating the distance that a surgical device has traveled along a guidewire adapted to be fixed to patient tissue, the distance indicator comprising:

an elongate housing having first and second housing ends longitudinally separated by a housing body and a guidewire connector, the guidewire connector being removably fasteneable to the guidewire to hold the housing stationary with respect thereto;

a plunger having first and second plunger ends longitudinally separated by a plunger body, the plunger being operatively connected to the housing for longitudinal motion with respect to the housing, and the first plunger end having a device engaging surface configured to operatively contact the surgical device; and a biasing member urging the plunger longitudinally with respect to the housing to keep the device engaging surface of the first plunger end in operative contact with the surgical device as the device moves with respect to the guidewire;

wherein, as the guidewire connector is holding the housing stationary with respect to the guidewire, the device engaging surface of the first plunger end is placed into operative contact with the surgical device with the plunger and housing in a first relative plunger/housing position, the surgical device moves longitudinally with respect to the guidewire and attached housing while the device engaging surface remains in operative contact therewith, and the plunger moves into a second relative plunger/housing position assisted by the operative connection between the first plunger end and the device, wherein the device engaging surface of the first plunger end remains spaced apart from the patient tissue to which the guidewire is adapted to be fixed in both of the first and second relative plunger/housing positions, the longitudinal difference between the first and second relative plunger/housing positions indicating a distance that the surgical device has moved longitudinally with respect to the guidewire.

2. The distance indicator of claim 1, wherein the guidewire connector includes a guidewire aperture extending at least a portion of the longitudinal distance therethrough, the guidewire aperture being configured to accept the guidewire and place the housing into a desired guidewire/housing position, the guidewire connector being configured to resist relative motion between the guidewire and the housing when the housing and guidewire are in the desired guidewire/housing position.

3. The distance indicator of claim 2, wherein the guidewire connector frictionally engages the guidewire to resist relative motion between the guidewire and the housing when the housing and guidewire are in the desired guidewire/housing position.

4. The distance indicator of claim 1, wherein the housing includes a plunger aperture extending from the first housing end into the housing body, the plunger aperture accepting the second plunger end and at least a portion of the plunger body and allowing relative motion of the plunger away from the second housing end as the biasing member urges the plunger from the first relative plunger/housing position to the second relative plunger/housing position.

5. The distance indicator of claim 1, wherein the housing includes a plunger aperture extending from the first housing end into the housing body, the plunger aperture accepting the second plunger end and at least a portion of the plunger body and allowing relative motion of the plunger toward the second housing end as the biasing member urges the plunger from the first relative plunger/housing position to the second relative plunger/housing position.

6. The distance indicator of claim 4, wherein the plunger aperture is in fluid communication with an outer surface of the housing through a viewing aperture extending substantially laterally through at least a portion of the housing body, the viewing aperture allowing a user to visualize a position of the plunger within the housing body.

7. The distance indicator of claim 5, wherein the plunger aperture is in fluid communication with an outer surface of the housing through a viewing aperture extending substantially laterally through at least a portion of the housing body, the viewing aperture allowing a user to visualize a position of the plunger within the housing body.

8. The distance indicator of claim 1, wherein at least one of the plunger and the housing includes an indicator scale configured to provide a quantitative indication of the longitudinal distance traveled by the plunger with respect to the housing during movement of the plunger from the first relative plunger/housing position to the second relative plunger/housing position.

9. An apparatus for monitoring movement of a medical device with respect to a guidewire connected to patient tissue, the guidewire having first and second guidewire ends longitudinally separated by a guidewire body, the first guidewire end contacting the patient tissue and the device being located longitudinally between the first and second guidewire ends and movably connected to the guidewire, the apparatus comprising:

an elongate housing having first and second housing ends longitudinally separated by a housing body, and a guidewire connector configured to accept at least one of the guidewire body and the second guidewire end to hold the housing stationary with respect thereto, the guidewire connector being removably fasteneable in place on the guidewire;

a plunger having first and second plunger ends longitudinally separated by a plunger body, the plunger being operatively connected to the housing for longitudinal motion with respect to the housing, and the first plunger end having a device engaging surface configured to operatively contact the medical device in a first relative plunger/housing position; and a biasing member urging the plunger longitudinally with respect to the housing to keep the device engaging surface of the first plunger end in operative contact with the medical device throughout a displacement of the medical device with respect to the guidewire, the biasing member being configured to move the plunger into a second relative plunger/housing position assisted by the operative connection between the first plunger end and the medical device, wherein the device engaging surface of the first plunger end remaining spaced apart from the patient tissue to which the guidewire is connected in both of the first and second relative plunger/housing positions, the longitudinal difference between the first and second relative plunger/housing positions indicating a distance that the medical device has moved longitudinally with respect to the guidewire.

10. The apparatus of claim 9, wherein the guidewire connector includes a guidewire aperture extending from the second housing end into the housing body, the guidewire aperture being configured to accept at least a portion of the guidewire and place the housing into a desired guidewire/housing position, the guidewire connector being configured to resist relative motion between the guidewire and the housing when the housing and guidewire are in the desired guidewire/housing position.

11. The apparatus of claim 9, wherein the guidewire connector frictionally engages the guidewire to resist relative motion between the guidewire and the housing when the housing and guidewire are in the desired guidewire/housing position.

12. The apparatus of claim 9, wherein the housing includes a plunger aperture extending from the first housing end into the housing body, the plunger aperture accepting the second plunger end and at least a portion of the plunger body and allowing relative motion of the plunger away from the second housing end as the biasing member urges the plunger from the first relative plunger/housing position to the second relative plunger/housing position.

13. The apparatus of claim 9 wherein the housing includes a plunger aperture extending from the first housing end into the housing body, the plunger aperture accepting the second plunger end and at least a portion of the plunger body and allowing relative motion of the plunger toward the second housing end as the biasing member urges the plunger from the first relative plunger/housing position to the second relative plunger/housing position.

14. The apparatus of claim 9, wherein at least one of the plunger and the housing includes an indicator scale configured to provide a quantitative indication of the longitudinal distance traveled by the plunger with respect to the housing during movement of the plunger from the first relative plunger/housing position to the second relative plunger/housing position.

\* \* \* \* \*